United States Patent [19]

Penaluna et al.

[11] Patent Number: 5,183,101
[45] Date of Patent: Feb. 2, 1993

[54] CIRCULATING CHILLER FOR ELECTRIFIED SOLUTIONS

[75] Inventors: William A. Penaluna, Pinole; Charles W. Ragsdale, Concord, both of Calif.

[73] Assignee: Bio-Rad Laboratories, Inc., Hercules, Calif.

[21] Appl. No.: 703,445

[22] Filed: May 21, 1991

[51] Int. Cl.$^5$ .................. F28F 21/00; F25D 17/02
[52] U.S. Cl. ....................... 165/47; 62/196.4; 62/435; 165/134.1; 165/104.33; 204/299 R
[58] Field of Search ............. 165/104.33, 134.1, 47; 204/299 R; 62/196.4, 435

[56] References Cited

U.S. PATENT DOCUMENTS

| | | | |
|---|---|---|---|
| 3,148,513 | 9/1964 | Ewing | 62/435 |
| 3,555,843 | 1/1971 | Cook | 62/196.4 |
| 3,616,455 | 10/1971 | Von Munchhausen | 204/299 R |
| 3,817,321 | 6/1974 | von Cube et al. | 165/104.33 |
| 4,362,612 | 12/1982 | Bier | 204/299 R |
| 4,368,448 | 11/1983 | Kobayashi et al. | 165/134.1 |
| 4,473,452 | 9/1984 | Cantor et al. | 204/180 G |
| 4,612,106 | 9/1986 | Kromer et al. | 204/299 R |
| 4,706,737 | 11/1987 | Taylor et al. | 165/47 |
| 4,737,251 | 4/1988 | Carle et al. | 204/182.8 |
| 4,802,338 | 2/1989 | Oswalt et al. | 62/196.4 |

FOREIGN PATENT DOCUMENTS 0047647  2/1988  Japan ................ 204/299 R

OTHER PUBLICATIONS

Nucleics Acids Research vol. 12, No. 14, 1984, "Separation of Chromosomal DNA Molecules From Yeast by Orthogonal-Field-Alternation Gel Electrophoresis" Carle & Olson.
Carle et al., *Nucleic Acid Res.* 12:5647–5664 (1984).
Gardiner et al., *Somat. Cell Molec. Genet.* 12:185–195 (1986).
Chu et al., *Science* 234:1592–1585 (1986).
Clark et al., *Science* 241:1203–1205 (1988).
Turmel et al., *Nucleic Acids Res.* 183:569–575 (1990).

*Primary Examiner*—John K. Ford

[57] ABSTRACT

A buffer solution being used in an electrophoresis cell as both an electrode buffer and a cooling medium is circulated through a refrigeration system external to the cell without risk of arcing or other danger despite the electrified state of the buffer solution. The refrigeration system contains a circulating coolant, a shell-and-tube heat exchanger, various components for the coolant such as a compressor, condenser and capillary, and preferably also a by-pass which, on command from a temperature control unit, passes warm coolant from the compressor discharge directly to the heat exchanger. Couplings of dielectric material insulate the heat exchanger from the remaining components of the refrigeration system.

9 Claims, 4 Drawing Sheets

CIRCULATING CHILLER FOR ELECTRIFIED SOLUTIONS

This invention lies in the field of heat exchange devices, and particularly laboratory liquid cooling apparatus for use in connection with electrophoresis systems.

BACKGROUND OF THE INVENTION

Temperature control is an important factor in achieving effective and reproducible results in electrophoretic separations, since the properties of the separation medium and the migration characteristics of the solutes both tend to vary when exposed to varying temperatures. Temperature variations occur as a result of the rise in temperature caused by the electrical resistance encountered by the current which drives the solute migration. The temperature rise is more pronounced in systems which utilize a relatively large volume of separation medium. Separations in media which fill slab-shaped and tube-shaped enclosures, for example, are more susceptible than those performed in capillary tubing where heat transfer through the capillary wall is generally sufficient to cool the medium. To avoid or minimize these variations, this temperature rise must be held in check.

In systems where heat transfer to the atmosphere alone does not provide sufficient cooling, one of the buffer solutions used to provide the electrical contact between the separation medium and the electrodes is also used as a heat transfer medium. For the buffer solution to serve both functions, a larger quantity is used than would otherwise be employed, the excess serving as a heat sink. Buffer solution heat sinks are commonly used with slab gels, where the flat faces of the slab gel enclosure provide a convenient contact area for heat transfer. In such arrangements, one or both of the electrode buffers is held in a chamber which not only contains the electrode and encloses one edge of the gel but also extends along the surface of one or both of the glass plates which form one side of the gel enclosure. To distribute the cooling over the entire gel face, the buffer solution is circulated or agitated within the chamber while a small portion of the buffer is refrigerated through a small segment of the chamber wall.

Cooling arrangements of this type are difficult to control, since only a small portion of the buffer solution is actually cooled and uniform mixing is difficult to achieve in the flat chambers which hold the solution against the glass plate. Electronic cooling devices have also been used, but these have been found to be less than fully satisfactory. Conventional approaches to circulating a coolant through a refrigeration system are not applicable to a buffer solution in an electrophoretic system since the buffer solution is electrified and raises a potential electrical hazard in the refrigeration equipment.

SUMMARY OF THE INVENTION

These and other concerns are addressed by the present invention, according to which an electrified buffer solution is circulated through a refrigeration system external to the electrophoresis cell and returned to the cell at a controlled low temperature, the refrigeration system constructed such that the housing and electrical units are maintained electrically insulated from the buffer solution. The buffer solution is thus cooled in its entirety in a circulating loop without any risk of arcing, equipment damage or injury to users in the vicinity.

Cooling of the electrified buffer solution is achieved by heat exchange with a refrigerant in a shell-and-tube heat exchanger, preferably in counter-current flow. The refrigerant is circulated and chilled by appropriate components of the apparatus, with couplings made of non-electrically conductive material situated in transfer tubing between the heat exchanger and the circulating and chilling components. In further embodiments, the heat exchanger is a coil of coaxial tubing arranged for passage of the buffer solution through the inner tubing and the refrigerant through the annular passage between the inner and outer tubing, the inner tubing being of a non-corrosive but heat-conducting metal. Mounting brackets securing the heat exchanger to the housing and to other components in the housing are also made of non-electrically conductive material, thereby electrically isolating the heat exchanger completely from the remaining components of the refrigeration system.

DETAILED DESCRIPTION OF THE INVENTION AND PREFERRED EMBODIMENTS

Figure 3:
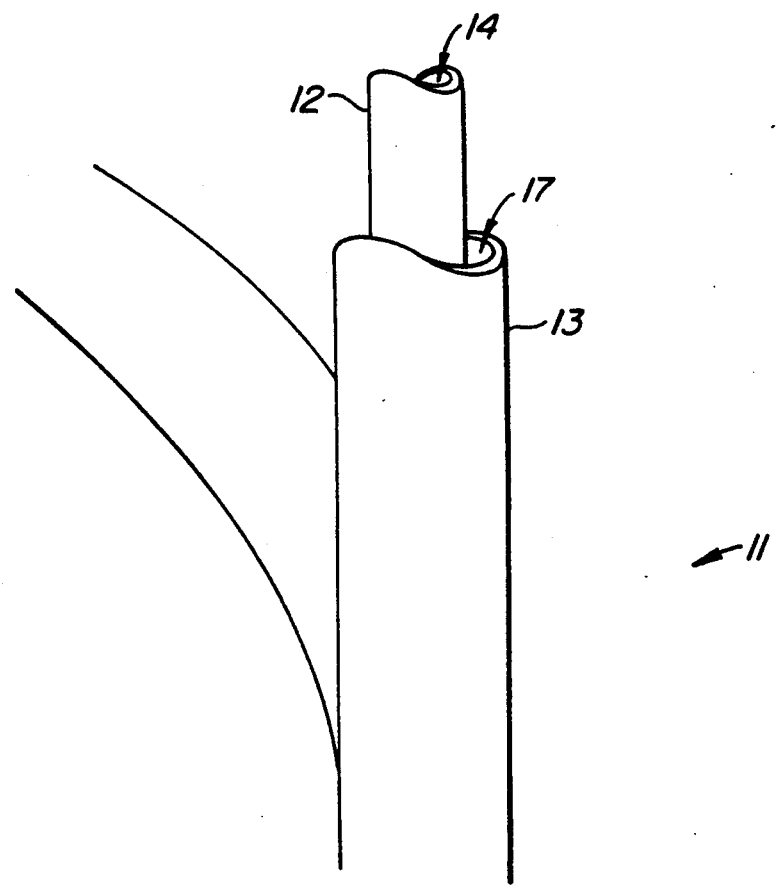
FIG. 3 is a view in partial cutaway of a segment of the heat exchanger which forms a part of the chiller module shown in FIGS. 1 and 2.
Figure 4:
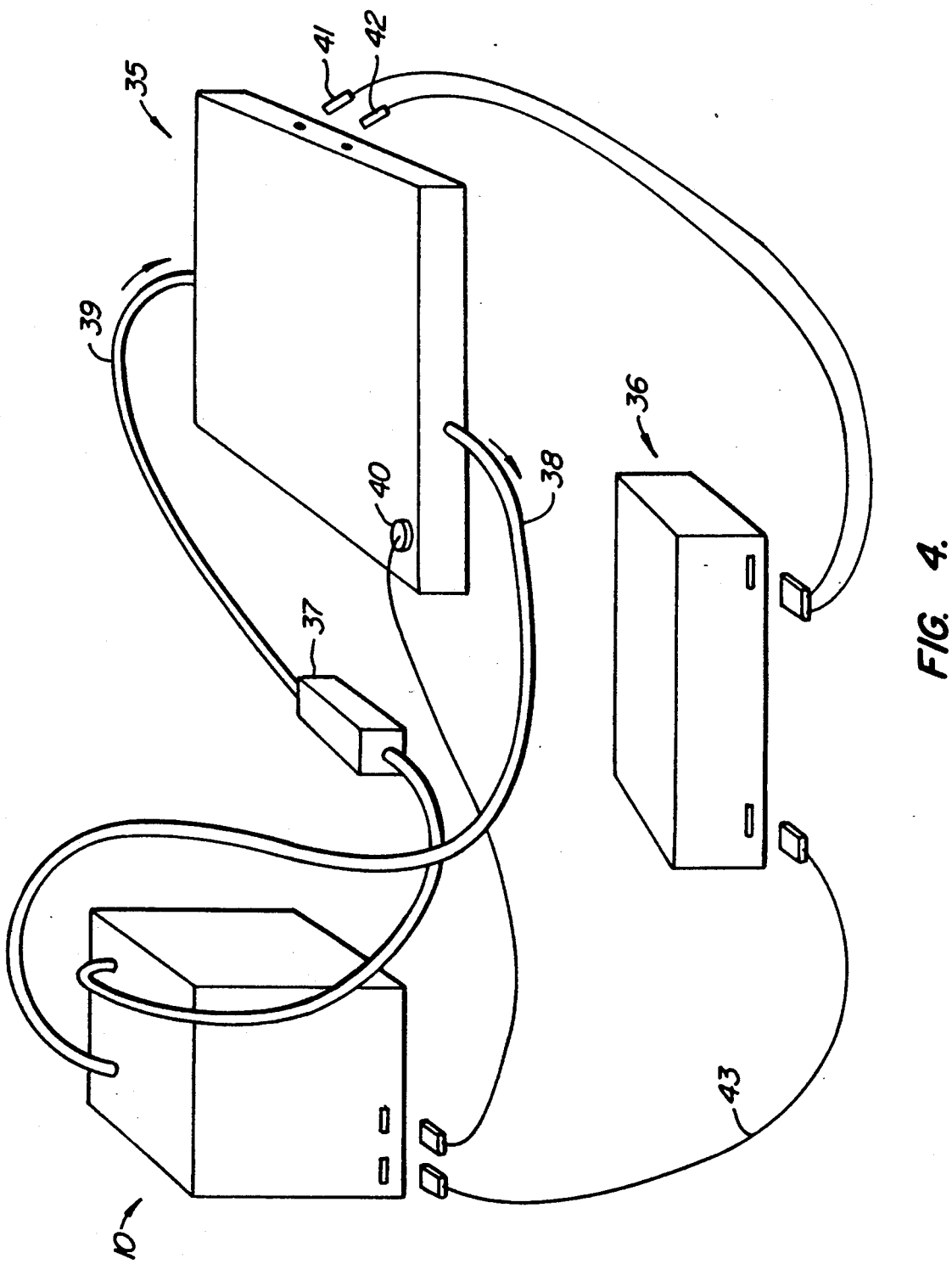
FIG. 4 is a depiction of the components of an electrophoresis system which incorporates the chiller module of FIGS. 1 and 2.

The structure and operation of the invention as a whole is most conveniently understood by a detailed review of one specific example. The Figures hereto depict one such example, FIGS. 1 and 2 representing a chiller module 10 which incorporates most of the components of the system, FIG. 3 showing the construction of the heat exchanger to indicate the flow passages, and FIG. 4 showing the chiller module as part of the electrophoresis system and apparatus as a whole.

Figure 1:
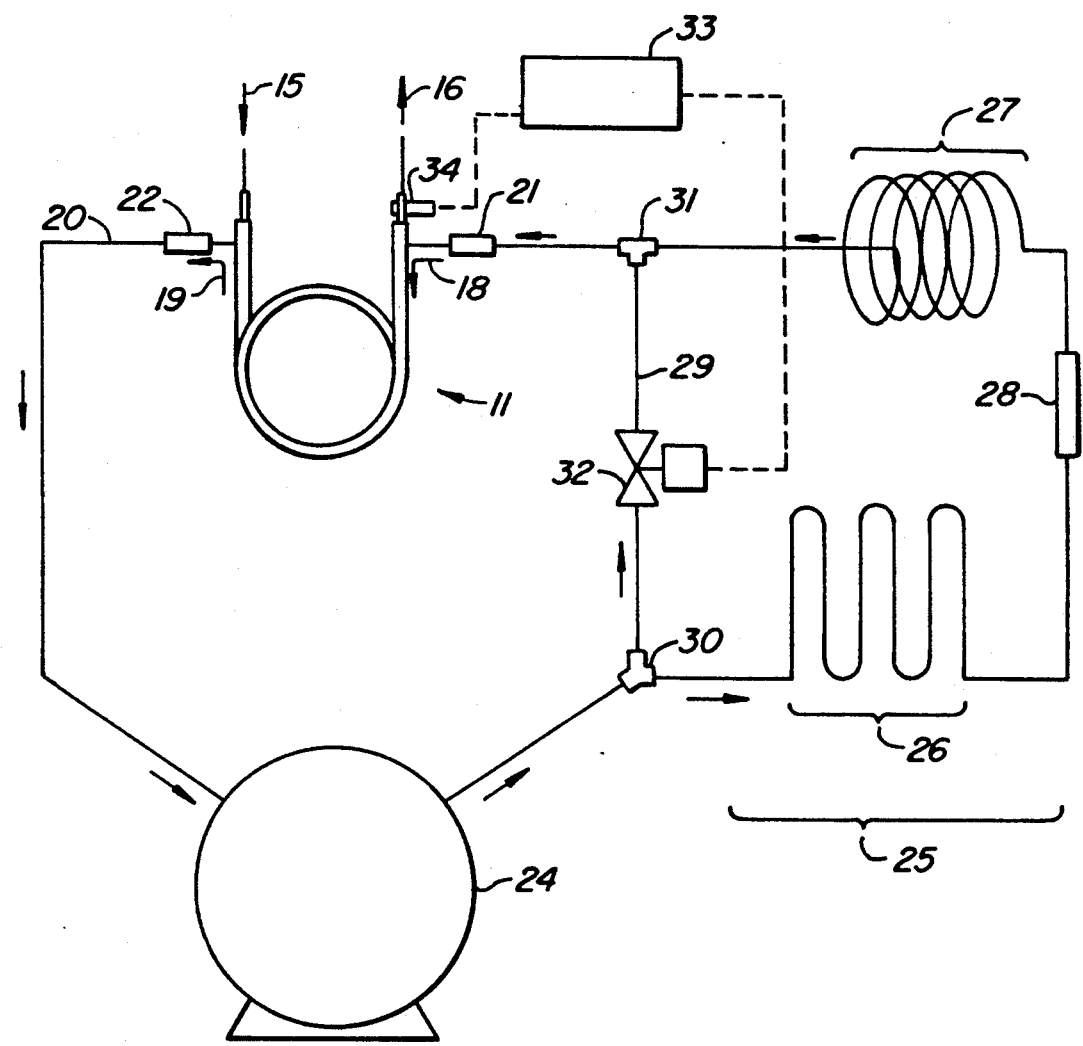
FIG. 1 is a flow diagram of the components of a chiller module incorporating features and components of the present invention.
Figure 2:
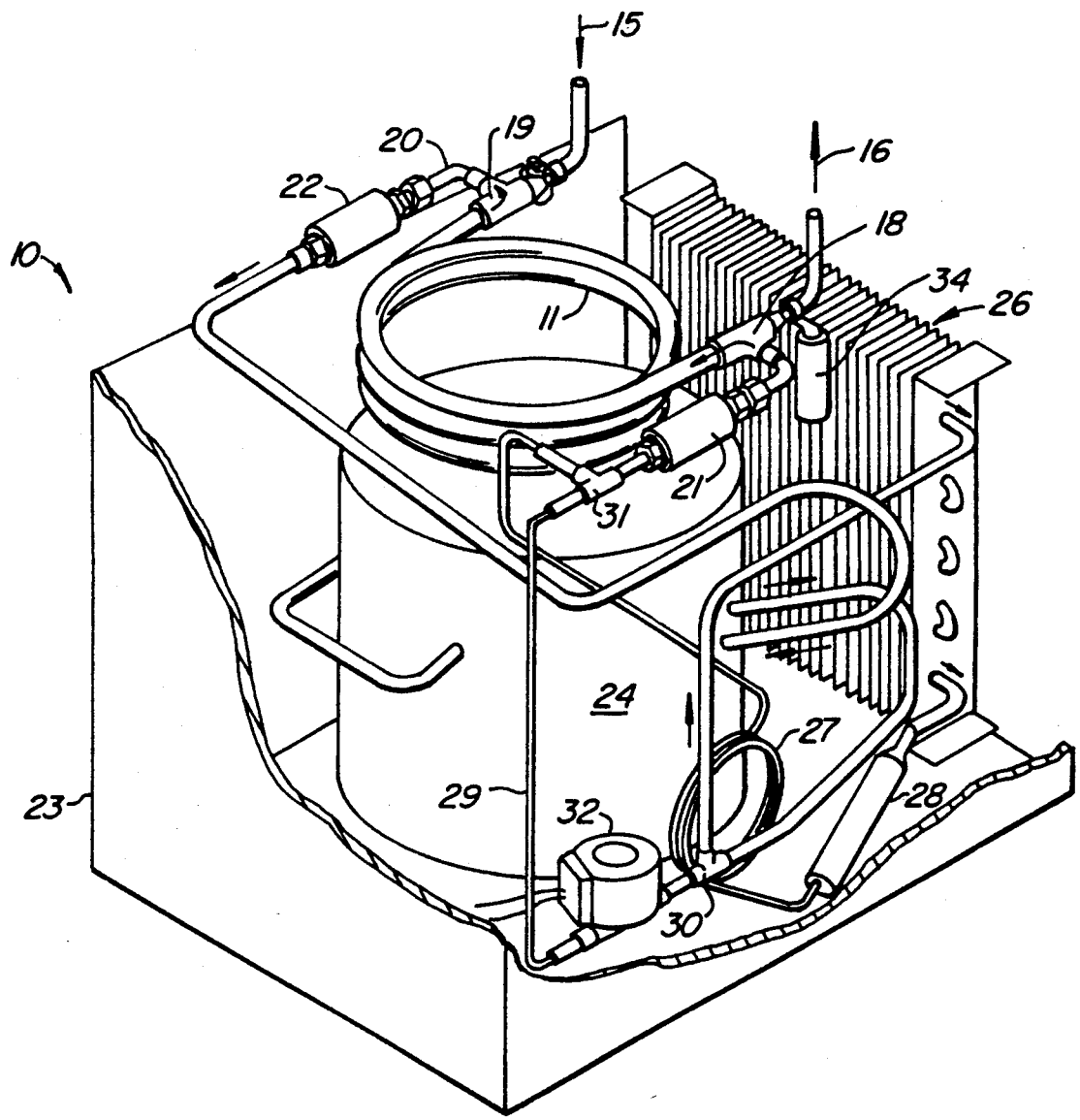
FIG. 2 is a perspective view in cutaway of the internal arrangement of components of the chiller module represented by the flow diagram of FIG. 1.

Looking at FIGS. 1 and 2 together, the components of the module can be seen in both a flow-sheet depiction (FIG. 1) and a depiction of both the appearance of the apparatus and the physical arrangement of the components in it (FIG. 2). The heat exchanger 11 is a coiled shell-and-tube heat exchanger, consisting of inner and outer coaxial tubing 12, 13, respectively (shown in detail in FIG. 3). Flow connections to the heat exchanger are arranged such that the buffer passes through the inner tubing 12 (i.e., the tube-side flow passage 14 of the heat exchanger) as indicated by the buffer inlet and outlet arrows 15, 16, respectively, while the coolant passes through the annular space between the inner and outer tubing (i.e., the shell-side flow passage 17) as indicated by the coolant inlet and outlet arrows 18, 19, respectively. The flows of buffer and coolant in this example are countercurrent, which is preferred for enhanced cooling efficiency. Alternative flow arrangements and exchanger constructions may be used as well, such as cocurrent flows and configurations other than coaxial tubing. The heat exchanger is coiled in this embodiment to achieve an economic use of space.

The inner tubing 12 of the heat exchanger is made of a material suitable for use with an electrified buffer solution. Corrosion-resistant heat-transfer tube material will enable the tubing to provide efficient heat transfer and yet withstand the wide range of buffer pH and composition which the tubing is likely to encounter. Metals are preferred, and stainless steels will serve well for this purpose.

The outer tubing 13 of the heat exchanger will be subject to fewer constraints, since it will not be in contact with the buffer solution. Any material which can be joined to the inner tubing material and retain a fluid-tight seal at high pressures can be used. Weldable materials capable of withstanding pressures up to 300 psi are preferred. Copper, aluminum, or other metals which are easily formed and welded to the inner tubing may be used. Copper for example can be welded to stainless steel in a manner capable of withstanding the conditions encountered in use by induction welding and other methods which will readily occur to those skilled in the art.

Transfer tubing 20 on either side of the heat exchanger 11 connects the shell-side flow passage with the remaining components of the chiller module. Couplings 21, 22 are positioned in the transfer tubing adjacent to the coolant inlet and outlet, respectively, of the heat exchanger. These couplings are of material which is not electrically conductive, and these couplings thereby insulate the outer tubing of the heat exchanger from the remainder of the tubing through which the coolant travels. Since the coolant itself will be of nonionic and non-electrically-conducting character, these couplings also electrically insulate the buffer solution from all remaining components of the chiller module 10 other than the heat exchanger. To fully insulate the buffer and heat exchanger, all mounting hardware securing the heat exchanger to other components of the chiller module and to the chiller module housing 23 will also be of non-electrically-conducting material. The actual material used for the couplings 21, 22 and the mounting hardware is not critical provided that it is electrically insulating and capable of withstanding the stress of cold temperatures. A wide variety of dielectric materials can be used. Polymeric materials such as polyvinyl chloride and other plastics are particularly convenient. Appropriate tube fittings for joining the couplings to the tubing may be molded or machined into the couplings at each end. Alternatively, metallic tube fittings may be fused or otherwise secured in a leak-proof manner to the dielectric coupling material at each end.

Coolant leaving the heat exchanger 11 and passing through the outlet dielectric coupling 22 enters a compressor 24 which compresses the coolant and drives the flow of the coolant through the system. The selection of an appropriate compressor is well within the routine knowledge of those skilled in the art, who in so doing will take into consideration such factors as the coolant used and the operating conditions such as flow rate, temperature change, and pressure change. One example of a compressor which will be suitable for freon coolants is a 1/12 hp CFC 12 compressor with overheat shut-down protection.

In the system shown, the coolant leaves the compressor 24 in gaseous form and passes through a chilling loop 25 which includes a condenser 26 and a capillary tube 27. The condenser 26 converts the pressurized gas to liquid form with a slight drop in temperature, and the capillary tube 27 causes a lowering of the pressure of the condensed coolant with an accompanying drop in temperature due to minimal heat exchange with the surroundings.

The condenser 26 can be any conventional piece of equipment with a capacity which suits the remaining components of the apparatus. The condenser shown in the drawing is a finned tube heat exchanger with the tubing turning at a 180° angle multiple times to form a parallel array of sections, the fins being perpendicular to each section. A typical condenser capacity which would be appropriate for the compressor referred to above is 650 BTU.

The capillary tube 27 can likewise be tubing of any conventional material capable of withstanding the pressure of the coolant. The length and internal diameter of the tubing will be selected to cause the desired pressure and temperature drop. A typical capillary tube is one with an internal diameter of 0.026 inch (0.066 cm) and a length of 72 inches (183 cm). These dimensions are not critical however and can be varied widely, depending on cooling conditions desired.

Interposed between the condenser 26 and the capillary tube 27 is a canister 28 containing a packed bed of pellets or other suitable material which serves as both a strainer of the coolant and a moisture remover.

The entire chilling loop 25 is bypassed by a by-pass line 29 joined to the chilling loop by two tees 30, 31. Passage through the by-pass line is controlled by a by-pass valve 32. This is an electrically operated open-close valve such as a solenoid valve, and is normally closed. The by-pass line serves as a means of controlling the temperature of the coolant entering the heat exchanger 11, by passing warm coolant from the discharge of the compressor 24 directly into the heat exchanger. The amount of warm coolant which will be passed through the by-pass line 29 is normally a small amount since the typical operation of the by-pass valve 32 will be an opening and closing in quick succession.

The operation of the by-pass valve 32 is governed by a controller 33 acting upon a signal from a temperature sensor 34 arranged to detect the temperature of the buffer leaving the heat exchanger 11. The temperature sensor 34 may be any conventional device capable of generating and emitting a signal representative of the buffer temperature. One example of such a device is a thermistor. The thermistor may serve additional functions as well, such as displaying both the preset and actual temperatures on a digital panel on the front of the chiller module housing. In any event, the controller 33 compares the temperature detected by the thermistor with the preselected set temperature, and operates the by-pass valve accordingly. The controller may be programmed to operate in any of various ways readily apparent to those skilled in the art to avoid excessive sensitivity. For example, the detected temperature may be averaged over a time period such as three minutes before compared to the set temperature, and the by-pass valve operated accordingly.

With the inclusion of the by-pass line 29 and by-pass valve 32 in the system, the compressor 24 is preferably a unit designed for continuous operation and will operate independently of the controller 33.

In one example of a typical mode of operation, the coolant leaving the heat exchanger will have a temperature of approximately 16° C., and this temperature may have risen to about 22° C. at the inlet of the compressor 24. The coolant is liquid up to this point, and leaves the compressor as a gas at a temperature of approximately 38° C. The coolant then cools down slightly to about 33° C. as it enters the condenser 26, and leaves the condenser as a liquid at about 26° C. The liquid coolant then passes through the packed bed canister 28 and the capillary tube 27 and leaves the capillary tube at a temperature of about 3° C., which is the temperature at which the coolant then enters the heat exchanger 11.

Turning next to FIG. 4, the chiller module 10 is shown as part of a complete system which also includes the electrophoresis cell 35, an electronic control unit 36 to supply power to the cell and control the voltage in the cell for specific applications, and a buffer circulation pump 37. Tubing for buffer circulation consists of tubing 38 drawing warm buffer from the cell 35 to the chiller module 10 and tubing 39 carrying chilled buffer from the chiller module 10 back to the cell 35. Additional electronic elements are a remote buffer thermistor 40 which monitors the buffer temperature in the cell itself and serves as an auxiliary means of temperature control for the chiller module, and electrode connections 41, 42. The latter are controlled by the control unit 36 which may also control the operations of the chiller module 10 through further connections 43. The buffer circulation pump may be any of a variety of pumps available in the industry, and the selection of a particular pump is not critical to the invention. In typical operation, the pump will circulate buffer at rate of about 1 liter per minute.

All components and materials used in the practice or implementation of this invention, within the limitations indicated above, may be conventional materials readily available and used for similar purposes in other equipment. The coolant, for example, may be any conventional coolant fluid designed for operation at temperatures in the temperature range indicated above. Freons are notable examples, although others will readily occur to those skilled in the art.

The chiller system and apparatus of the present invention are applicable for use in any electrophoresis system which utilizes one or both of the buffer solutions to maintain temperature control of the gel. Slab gel systems, including both vertically and horizontally arranged slabs, are prime examples. The invention is also of use in electrophoretic procedures involving complex electronic arrangements such as field alternation and switching. Examples are the various pulsed field electrophoretic process known in the art, such as the pulsed field gel electrophoresis (PFGE) system described by Cantor, et al., U.S. Pat. No. 4,473,452, the orthogonal field alternation gel electrophoresis (OFAGE) system described by Carle, G. F., and Olson, M. V., in Nucleic Acid Res. 12:5647-5664 (1984), the field-inversion gel electrophoresis (FIGE) system described by Carle, et al., U.S. Pat. No. 4,737,251, the transverse alternating field electrophoresis (TAFE) system described by Gardiner, K., Lass, W., and Patterson, D., in Somat. Cell Molec. Genet. 12:185-195 (1986), the contour-clamped homogeneous electric field (CHEF) system described by Chu, G., Vollrath, D., and Davis, R. W., in Science 234:1592-1585 (1986), the programmable autonomous control electrode (PACE) system described by Clark, S. M., Lai, E., Birren, B. W., and Hood, L., in Science 241:1203-1205 (1988), and the zero integrated field inversion (ZIFE) system described by Turmel, C., Brassard, E., Slater, G. W., and Noolandi, J., in Nucleic Acids Res. 183:569-575 (1990). The disclosures of each of these documents are incorporated herein by reference.

Control of the electrodes in accordance with one or more of these methods may be achieved by the control unit 36 shown in FIG. 4. One example of a control unit which will serve this purpose is the CHEF mapper of Bio-Rad Laboratories, Hercules Calif.

The foregoing is offered primarily for purposes of illustration. Further alternatives, variations and modifications will be apparent to those skilled in the art and can be substituted or incorporated without departing from the spirit and scope of the invention.

What is claimed is:

1. Apparatus for cooling an electrified buffer solution, comprising:
   a shell-and-tube heat exchanger having tube-side and shell-side flow passages separated by corrosion-resistant heat-transfer tube material;
   buffer circulating means for circulating said electrified buffer solution through said tube-side flow passage;
   coolant circulating means for circulating coolant through said shell-side flow passage;
   chilling means for chilling coolant thus being circulated, after its exit from said heat exchanger and prior to its reentry;
   transfer tubing connecting said shell-side flow passage with said coolant circulating means and said chilling means; and
   non-electrically-conductive couplings in said transfer tubing electrically isolating said heat exchanger from said coolant circulating means and said chilling means.

2. Apparatus in accordance with claim 1 in which said shell-and-tube heat exchanger is comprised of inner and outer concentric tubing, said inner tubing being of substantially non-corrosive metal, and said outer tubing and said transfer tubing both being of metal.

3. Apparatus in accordance with claim 1 in which said shell-and-tube heat exchanger is comprised of inner and outer substantially coaxial tubing, said inner tubing being of substantially non-corrosive metal and said outer tubing and said transfer tubing both being of metal, and said non-electrically-conductive couplings being of polymeric material.

4. Apparatus in accordance with claim 1 in which said heat exchanger, said buffer circulating means, said chilling means and said transfer tubing are mounted in a common housing, and said heat exchanger is isolated from said housing and all other components therein by non-electrically-conductive mounting fixtures.

5. Apparatus in accordance with claim 1 in which said shell-and-tube heat exchanger is defined as first heat exchange means, and said chilling means is comprised of:
   compressor means for raising the temperature and pressure of said coolant;
   second heat exchange means for lowering the temperature of coolant thus compressed, by heat exchange with surrounding atmosphere; and
   pressure lowering means for further lowering the temperature of said coolant thus cooled by said heat exchange means, by lowering the pressure thereof.

6. Apparatus in accordance with claim 5 further comprising:

temperature detection means for detecting the temperature of said electrified buffer solution at a point downstream of said first heat exchange means;

a by-pass line connecting said compressor means and said heat exchanger, by-passing said second heat exchange means and said pressure lowering means;

a valve in said by-pass line controlled by said temperature detection means; and control means for comparing the temperature detected by said temperature detection means with a preselected temperature, and for controlling the opening and closing of said valve in response thereto.

7. Apparatus for cooling an electrified buffer solution, comprising:

first heat exchange means comprising a shell-and-tube heat exchanger having tube-side and shell-side flow passages separated by corrosion-resistant heat-transfer tube material, said shell-side flow passage having an inlet port and an outlet port;

buffer circulating means for circulating said electrified buffer solution through said tube-side flow passage;

single compressor and circulation means for circulating coolant through said shell-side flow passage and for raising the temperature and pressure of, and vaporizing, said coolant upon leaving said shell-side flow passage;

second heat exchange means for lowering the temperature of, and condensing, coolant thus vaporized by said single compressor and circulation means, by heat exchange with surrounding atmosphere;

pressure lowering means for further lowering the temperature of said coolant thus condensed, by lowering the pressure thereof; and a first non-electrically-conductive coupling electrically isolating said outlet port of said shell-side flow passage from said single compressor and circulation means, and a second non-electrically-conductive coupling electrically isolating said inlet port of said shell-side flow passage from said pressure lowering means.

8. Apparatus in accordance with claim 7 further comprising:

temperature detection means for detecting the temperature of said electrified buffer solution at a detection point downstream of said first heat exchange means;

a by-pass line connecting the outlet of said single compressor and circulation means with said inlet port of said shell-side flow passage of said first heat exchange means, by-passing said second heat exchange means and said pressure lowering means;

an on-off valve in said by-pass line; and control means for comparing the temperature detected by said temperature detection means with a preselected temperature, and for controlling the opening and closing of said valve in response thereto, thereby regulating the temperature of said electrified buffer solution at said detection point.

9. Apparatus in accordance with claim 8 in which said single compressor and circulation means is constructed to operate continuously only, independent of said control means.

* * * * *